United States Patent [19]

Daicho et al.

[11] Patent Number: 5,374,663
[45] Date of Patent: Dec. 20, 1994

[54] PROCESS FOR PRODUCING CYANOPSIA-CORRECTABLE INTRAOCULAR LENS

[75] Inventors: Masanori Daicho, Kodama; Yuuichi Yokoyama, Kounosu; Makoto Tsuchiya, Honjo, all of Japan

[73] Assignee: Hoya Corporation, Tokyo, Japan

[21] Appl. No.: 7,027

[22] Filed: Jan. 21, 1993

Related U.S. Application Data

[63] Continuation of Ser. No. 815,611, Jan. 7, 1992, abandoned, which is a continuation of Ser. No. 432,758, filed as PCT/JP89/00230, Mar. 3, 1989, abandoned.

[30] Foreign Application Priority Data

Mar. 3, 1988 [JP] Japan ............................ 63-50394

[51] Int. Cl.$^5$ ............................................. A61L 27/00
[52] U.S. Cl. ................................. 523/106; 351/162; 623/6; 514/912; 514/972
[58] Field of Search ................ 351/162; 523/106; 623/6; 514/912, 972

[56] References Cited

U.S. PATENT DOCUMENTS

| | | | |
|---|---|---|---|
| 4,102,567 | 7/1978 | Cuffe et al. | 351/162 |
| 4,260,768 | 4/1981 | Lorenz et al. | 526/259 |
| 4,328,148 | 5/1982 | Kuzma | 523/106 |
| 4,390,676 | 6/1983 | Loshack | 351/160 H |
| 4,559,059 | 12/1985 | Su | 351/162 |
| 4,795,461 | 1/1989 | Lundquist et al. | 523/106 |
| 4,863,466 | 9/1989 | Schlegel | 351/162 |
| 4,921,205 | 5/1990 | Drew, Jr. et al. | 264/1.7 |

FOREIGN PATENT DOCUMENTS 2255901 11/1987 Japan .................................. 351/177

OTHER PUBLICATIONS

CA 110(12): 96748p, May 1988 (Frontini).

Primary Examiner—Paul R. Michl
Assistant Examiner—Andrew E. C. Merriam
Attorney, Agent, or Firm—Nixon & Vanderhye

[57] ABSTRACT

The present invention relates to a process for producing a cyanopsia-correctable intraocular lens, which process is characterized by, in polymerizing a monomer capable of forming a transparent lens material upon polymerization to obtain an intraocular lens, adding, as an essential component, at least one member of yellow, yellowish brown and orange colorants and, as an optional components, an U.V. absorber and a crosslinking monomer. The intraocular lens obtained by the present invention has a light absorption characteristic close to that of human crystalline lens and is effective for correction of cyanopsia.

16 Claims, 5 Drawing Sheets

F I G. 1
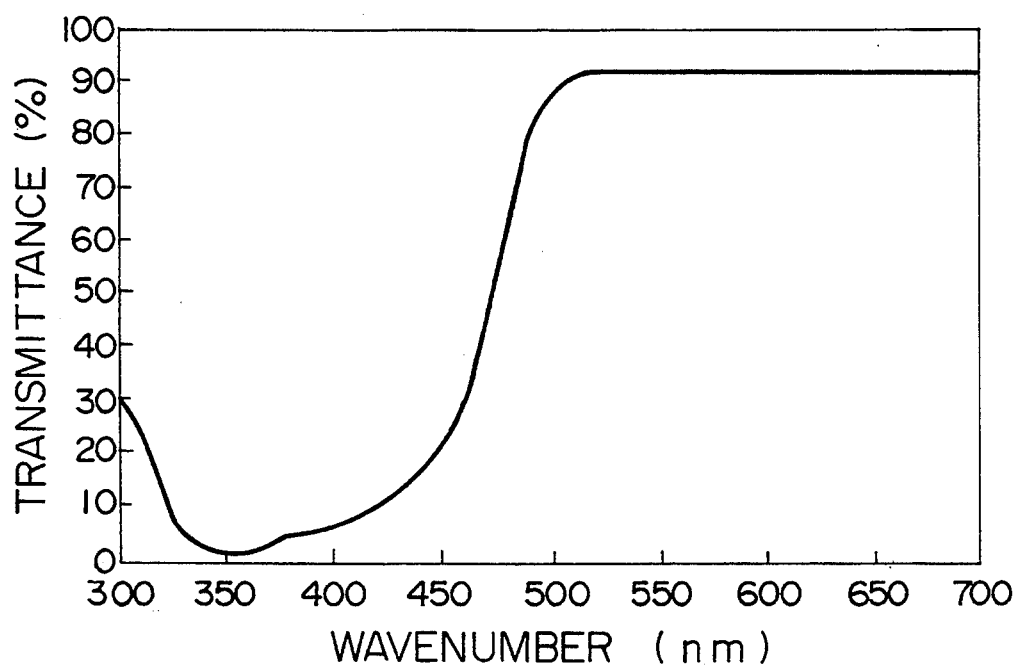
F I G. 2
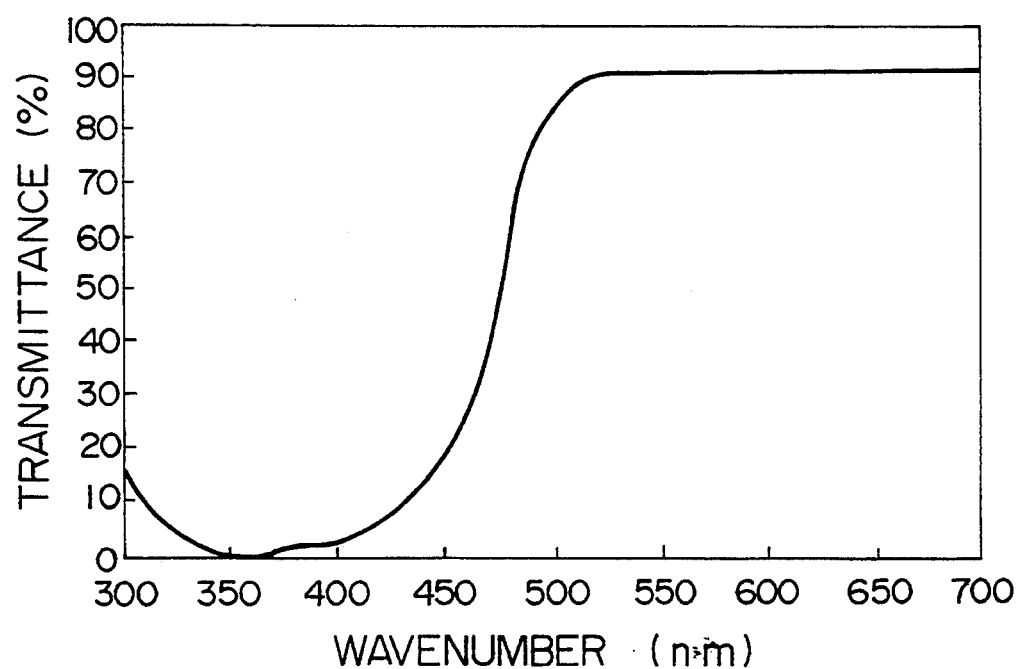

PROCESS FOR PRODUCING CYANOPSIA-CORRECTABLE INTRAOCULAR LENS

This is a continuation of application Ser. No. 07/815,611, filed Jan. 7, 1992, now abandoned, which is a continuation of 07/432,758, filed as PCT/JP89/00230, Mar. 3, 1989, now abandoned.

TECHNICAL FIELD

The present invention relates to a process for producing a cyanopsia-correctable intraocular lens and particularly to a process for producing an intraocular lens for correction of the cyanopsia which arises in aphakic eye patients after operation of cataract.

BACKGROUND ART

In recent years, with the increase in population of old people, patients of senile cataract have increased. In aphakic eye patients whose crystalline lens(es) has (have) been enucleated by operation of cataract, the correction for eyesight is generally effected by the use of any of spectacles, contact lenses and intraocular lenses.

In effecting the above eyesight correction by spectacles, the lenses for correction are thick convex lenses having an unattractive appearance, and the image formed on the retina is larger than that in normal eyes. Accordingly, particularly when one eye is aphakic, there arises aniseikonia, thus making larger the fatigue of optic nerve and cranial nerves and giving a big burden to the spectacles users.

Hence, in recent years, there have been developed contact lenses which are superior in oxygen supply to the cornea and which give a smaller burden to the cornea even when worn for a long time, thus providing a very effective means for eyesight correction in aphakic eye patients.

Further, there have been developed intraocular lenses which are implanted into eyes and accordingly require no detachment, and these lenses are gaining acceptance in the market. The intraocular lenses, as compared with the above mentioned spectacles, etc., have many advantages and are expected to further spread in the future.

Incidentally, many of the aphakic eye patients after cataract operation complain of glare, a difference of color vision, etc. In particular, cyanopsia in which objects look bluish is known generally. Cyanopsia is a disease in which, owing to the removal of the crystalline lens(es) originally having an yellow to yellowish brown color, a blue light (a complementary color to an yellow to yellowish brown color) reaches the retina without being weakened and consequently objects look more blue than in normal eyes. Even when artificial intraocular lenses of conventional type have been implanted into eyes, a blue light reaches the retina without being weakened, in the case of eyes implanted with posterior chamber intraocular lenses made of polymethyl methacrylate (PMMA). Consequently there is seen reduction in distinguishability between blue to bluish violet colors, as compared with the case of phakic eyes.

Hence, intraocular lenses capable of correcting cyanopsia are desired, and U.V. absorber-containing intraocular lenses have been commercialized in order to allow the lenses to have a light absorption characteristic close to that originally possessed by human crystalline lenses. However, U.V. absorbers show a very low absorption in a visible light region and is unable to absorb a visible blue light, though they can absorb an U.V. light of 400 nm or less regarded to be a harmful wavelength; therefore, with the U.V. absorber-containing intraocular lenses, the correction of cyanopsia is incomplete. When a large amount of an U.V. absorber is used in an intraocular lens in order to allow the lens to have an increased absorption in a visible light region, other properties of lens material are decreased or worsened in many cases, which is not preferable.

Incidentally, a so-called prepolymer process is known as a process for producing the U.V. absorber-containing intraocular lens mentioned above. In this prepolymer process, a monomer solution comprising a monomer capable of forming a transparent lens material upon polymerization, an U.V. absorber and a polymerization initiator is introduced into a reactor and then heated for a given length of time at a given temperature to obtain a prepolymer of high viscosity; thereafter, the prepolymer is filtered through a filter, casted into a cell constituted by, for example, two glass plates and a gasket, and then further heated for a given length of time at a given temperature to obtain a transparent lens material.

This prepolymer process has such advantages that the prepolyemr casted into the cell scarcely leaks out therefrom because of its high viscosity and that the shrinkage degree in the step of obtaining a transparent lens material from the prepolymer is small, enabling the production of a transparent lens material having a desired shape. On the other hand, the prepolymer process has problems such as (i) polymerization is effected in two steps thereby making the operation complicated, (ii) the control of the polymerization degree and viscosity of the prepolymer obtained in the first polymerization step is difficult; for example, when the polymerization degree is high and resultantly the prepolyemr viscosity is high, the filtration treatment of the prepolymer conducted before its casting into the cell is difficult (the filtration treatment of the prepolymer of high viscosity is extremely difficult particularly when there is used, for example, a filter of $0.2\mu$ in pore diameter in order to remove not only dust but also bacteria), and (iii) when a crosslinking monomer is used in order to allow the polymer obtained to have a hardness, etc., an insoluble polymer is formed in the step of obtaining a prepolymer and the filtration treatment becomes difficult also in this case, and further an insoluble polyemr is formed even in the step of polymer production after the filtration treatment and the polymer obtained (an intraocular lens material) becomes non-uniform.

Hence, an object of the present invention is to provide a process for producing a cyanopsia-correctable intraocular lens, which lens is able to eliminate the drawbacks of conventional intraocular lenses containing an U.V. absorber and can effectively correct the cyanopsia arising in aphakic eye patients after operation of cataract.

Further, another object of the present invention is to provide a process for producing a cyanopsia-correctable intraocular lens, which process is able to obtain smoothly without conducting a complicated operation, an intraocular lens capable of effectively correcting the above cyanopsia.

DISCLOSURE OF THE INVENTION

The present inventors made investigation in order to achieve the above objects and, as a result, found that an intraocular lens having a light absorption characteristic close to that of human crystalline lens and being effective for correction of cyanopsia can be obtained by a monomer cast polymerization process in which a monomer solution comprising a polymerizing monomer as shown below, a particular colorant and a polymerization initiator is casted into a mold and polymerized in a single step. The present inventors further found that the monomer cast polymerization process can be conducted in a simple operation as compared with the above mentioned prepolymer process in which polymerization is effected in two steps, and that the intraocular lens obtained is uniform.

Therefore, the present invention resides in a process for producing a cyanopsia-correctable intraocular lens by monomer cast polymerization, which process is characterized by comprising steps of casting into a mold a monomer solution comprising at least one monomer capable of forming a transparent lens material upon polymerization, at least one colorant selected from yellow, yellowish brown and orange colorants, and a polymerization initiator; sealing the mold; and effecting polymerization.

According to the present invention, by further adding an U.V. absorber to the monomer solution, there can be obtained an intraocular lens having a light absorption characteristic closer to that of human crystalline lens and accordingly being very effective for correction of cyanopsia.

According to the present invention, by further adding a crosslinking monomer to the monomer solution there can be obtained an intraocular lens superior in hardness, solvent resistance, resistance to YAG laser beam, etc.

According to the present invention, by selecting an azo type polymerization initiator as said polymerization initiator, there can be obtained an intraocular lens which reduces the significant fading of colorant often arising when using a peroxide type polymerization initiator and accordingly is stable chemically.

BRIEF DESCRIPTION OF DRAWINGS

FIGS. 1–8 are graphs showing the light transmittance curves of cyanopsia-correctable intraocular lenses obtained according to the present invention.

BEST MODE FOR CARRYING OUT THE INVENTION

Figure 3:
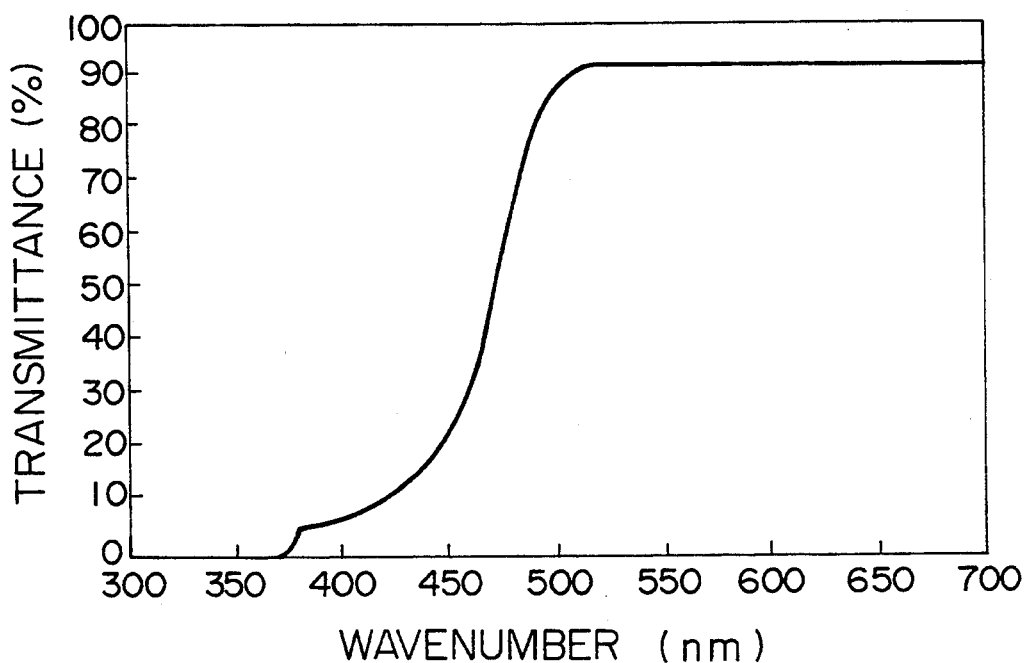
Figure 4:
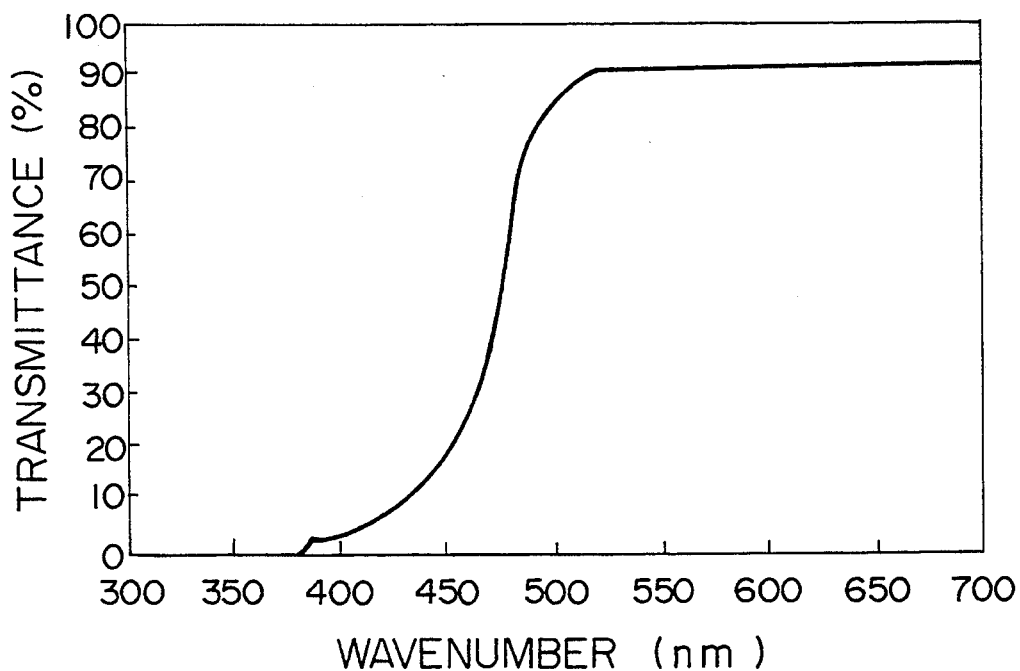
Figure 5:
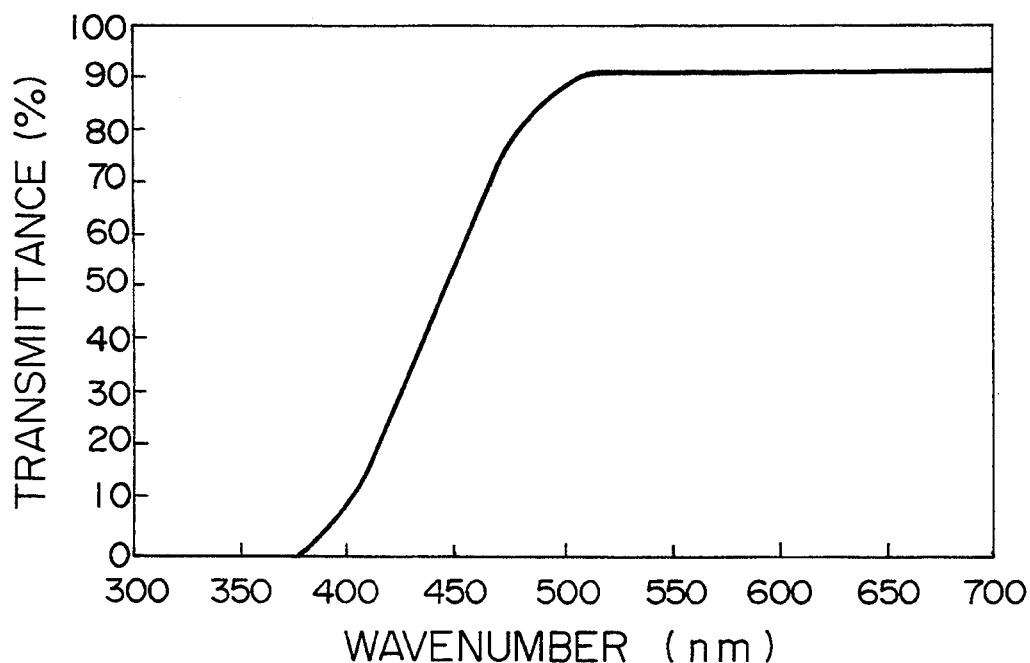
Figure 6:
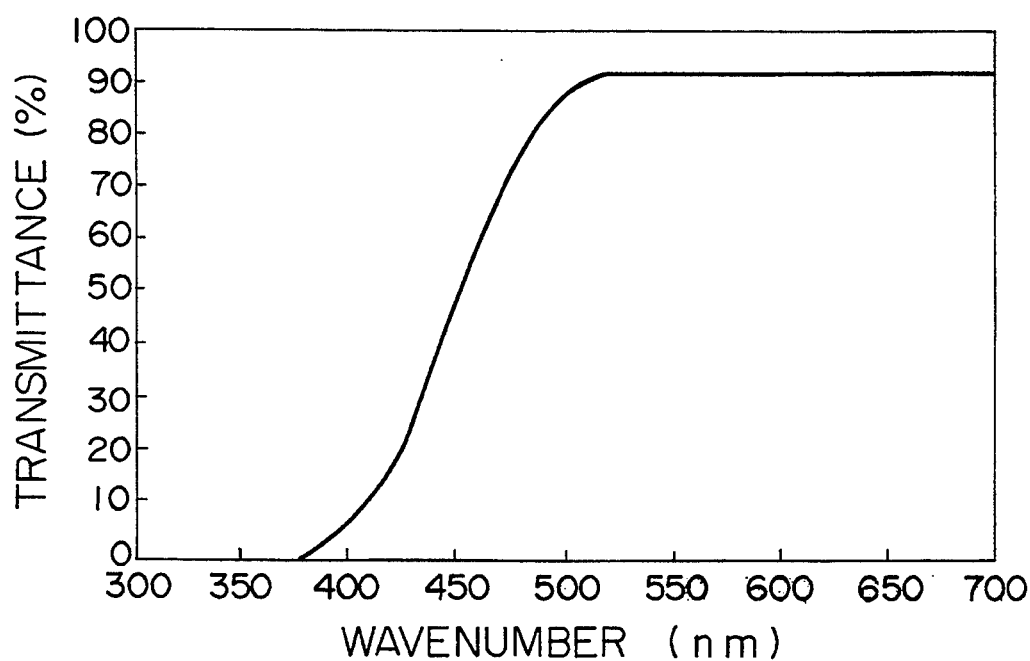
Figure 7:
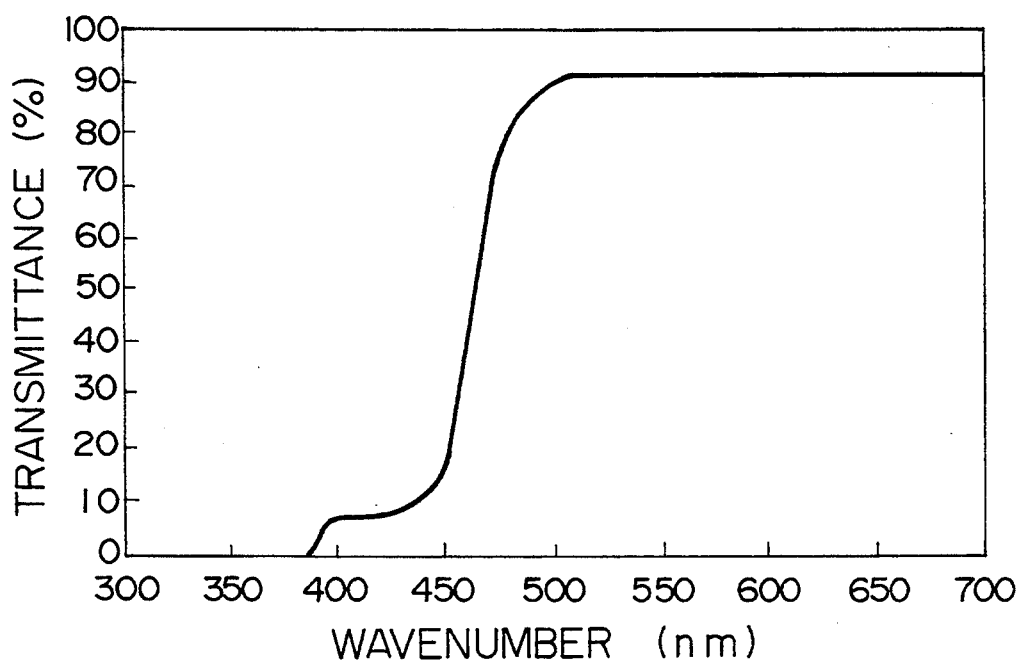

In the process of the present invention for producing a cyanopsia-correctable intraocular lens, there is firstly prepared a monomer solution comprising at least one monomer capable of forming a transparent lens material upon polymerization, at least one colorant selected from yellow, yellowish brown and orange colorants and a polymerization initiator.

As the monomer capable of forming a transparent lens material upon polymerization, there are preferably used (meth)acrylic acid esters obtaiend from (meth)acrylic acid and alkanols of 1–6 carbon atoms (methanol, ethanol, propanol, butanol, heptanol, hexanol). Incidentally, the "(meth)acrylic acid" used herein means both of acyclic acid and methacrylic acid. A particularly preferable (meth)acrylic acid ester is methyl methacrylate. However, the monomer used in the present invention is not restricted to the (meth)acrylic acid esters, and there can also be used other monomers as long as they can form a transparent lens material upon polymerization. As these monomers, there can be mentioned, for example, (i) vinyl group-containing monomers such as styrene, vinyl acetate and the like, (ii) alkyl esters of unsaturated carboxylic acids such as itaconic acid, fumaric acid, maleic acid and the like, (iii) unsaturated carboxylic acids such as methacrylic acid, acrylic acid, itaconic acid, fumaric acid, maleic acid and the like, (iv) fluorine-containing monomers such as fluoro(meth)acrylate and the like and (v) silicone-containing monomers.

The monomers can be used alone or in two or more. When two or more monomers are used, they may be a mixture of monomers selected from (meth)acrylic acid esters, or a mixture of a (meth)acrylic acid ester and other monomer as mentioned above.

The monomer solution further comprises, as an essential component, at least one colorant selected from yellow, yellowish brown and orange colorants. As the yellow colorants, although they are not restricted to the followings, there can be mentioned C.I. (Color Index) Solvent Yellow 16, C.I. Solvent Yellow 29, C.I. Solvent Yellow 33, C.I. Solvent Yellow 44, C.I. Solvent Yellow 56, C.I. Solvent Yellow 77, C.I. Solvent Yellow 93, C.I. Disperse Yellow 3, etc. Also as the yellowish brown colorants, although they are not restricted to the followings, there can be mentioned C.I. Solvent Yellow 14, C.I. Solvent Yellow 104, C.I. Solvent Yellow 105, C.I. Solvent Yellow 110, C.I. Solvent Yellow 112, C.I. Solvent Yellow 113, C.I. Solvent Yellow 114, etc. Further as the orange colorants, although they are not restricted to the followings, there can be mentioned C.I. Solvent Orange 60, C.I. Solvent Orange 67, C.I. Solvent Orange 68, C.I. Solvent Orange 79, C.I. Solvent Orange 80, C.I. Solvent Orange 86, C.I. Disperse Orange 47, etc.

These colorants can be used alone or in two or more of the same or different colors.

These colorants show the maximum absorption at a wavelength of 320–450 nm and can absorb a visible blue light and an U.V. light, whereby the intraocular lens obtained is endowed an effect for correction of cyanopsia. The use of an yellow colorant showing the maximum absorption at a wavelength of 350–400 nm is particularly preferable.

When only the colorant is used without using an U.V. absorber as mentioned later, the amount of colorant used is preferably 0.01–0.05% (W/V) based on total monomer amount. The reason is that when the amount is less than 0.01% (W/V), the resulting intraocular lens shows an insufficient absorption and, when the amount is more than 0.05% (W/V), the resulting intraocular lens has a light absorption characteristic different from that of human crystalline lens.

The monomer solution furthermore comprises a polymerization initiator as an essential component. As the polymerization initiator, there can be used various polymerization initiators such as azo type polymerization initiators, peroxide type polymerization initiators and the like. The use of an azo type polymerization initiator is particularly preferable. The reason is that (i) when an azo type polymerization initiator is used in the process of the present invention for producing a cyanopsia-correctable intraocular lens by monomer cast polymerization, the addition amount can be small as compared with when a peroxide type polymerization initiator is used (for example, 2,2'-azobisisobutyronitrile which is an azo type polymerization initiator is sufficient at an amount of 0.1% by weight while benzoyl peroxide which is a peroxide type polymerization initiator is used in an amount of 0.4% by weight), moreover, the amount of the decomposition product of the polymerization initiator remaining in the polymer obtained can be made small, as a result, a chemically stable intraocular lens can be obtained, and (ii) while the peroxide type polymerization initiator has a bleaching action and may cause, for example, the fading of the colorant coexisting in the monomer solution, the azo type polyemrization initiator seldom causes such a problem.

As specific examples of the azo type polymerization initiator, there can be mentioned 1,1'-azobis(cyclohexane-1-carbonitrile), 2,2'-azobisisobutyronitrile, 2,2'-azobis(2,4-dimethylvaleronitrile), 2,2'-azobis(4-methoxy-2,4-dimethylvaleronitrile), dimethyl 2,2'-azobisisobutyrate, etc. The amount of azo type polymerization initiator used is preferably 0.001–1.0% (W/W) based on total monomer amount. The reason is that when the amount is less than 0.001% (W/W), the polymerization is insufficient and non-uniform and, when the amount is more than 1.0% (W/W), foaming may occur.

The monomer solution can comprise U.V. abosrber if necessary. The use of the U.V. absorber in combination with the colorant can control the absorption of a light of 300–500 nm at a desired level. Therefore, by selecting the type and addition concentration of colorant so that the resulting intraocular lens can have a visible region absorption characteristic close to that of an individual human crystalline lens and further by supplementing the shortage of U.V. region absorption by the U.V. absorber, the resulting intraocular lens can have a light absorption characteristic closer to that of human crystalline lens.

When the U.V. absorber is used together with the colorant, the amount of colorant used can be 0.01–0.03% (W/V) based on total monomer amount and the amount of U.V. absorber used can be 0.03–0.05% (W/V). That is, in the intraocular lenses of prior art using an U.V. absorber alone without colorant, no light absorption characteristic curve close to that of human crystalline lens can be obtained even when the U.V. absorber is used in an amount of 0.3–0.5% (W/V), but in the intraocular lens obtained according to the present invention, the object can be achieved even when the total amount of the colorant and the U.V. absorber is as samll as 1/5 or less of the amount of U.V. absorber used in the intraocular lenses of prior art.

As such an U.V. absorber, there can be mentioned, for exmaple, the followings.

Benzotriazole type
  2-(2'-Hydroxy-5'-methylphenyl)benzotriazole (for example, Tinuvin P, manufactured by Ciba-Geigy Corp.)
  2-(2'-Hydroxy-5'-tert-butylphenyl)benzotriazole
  2-(2'-Hydroxy-3',5'-di-tert-butylphenyl)benzotriazole
  2-(2'-Hydroxy-3'-tert-butyl-5'-methylphenyl)-5-chlorobenzotriazole (for example, Tinuvin 326, manufactured by Ciba-Geigy Corp.)
  2-(2'-Hydroxy-3',5'-di-tert-butylphenyl)-5-chlorobenzotriazole
  2-(2'-Hydroxy-3',5'-di-tert-amylphenyl)benzotriazole
  2-(2'-Hydroxy-4'-octoxyphenyl)benzotriazole Salicylic acid type
  Phenyl salicylate
  p-tert-Butylphenyl salicylate
  p-Octylphenyl salicylate Benzophenone type
  2,4-Dihydroxybenzophenone
  2-Hydroxy-4-methoxybenzophenone
  2-Hydroxy-4-octoxybenzophenone
  2-Hydroxy-4-dodecyloxybenzophenone
  2,2'-Dihydroxy-4-methoxybenzophenone
  2,2'-Dihydroxy-4,4'-dimethoxybenzophenone
  2-Hydroxy-4-methoxy-5-sulfobenzophenone Cyanoacrylate type
  2-Ethylhexyl-2-cyano-3,3'-diphenylacrylate
  Ethyl-2-cyano-3,3'-diphenylacrylate The monomer solution can comprise further a crosslinking monomer if necessary. By using this crosslinking monomer, the resulting intraocular lens can have an improved hardness and improved solvent resistance. After the transplant of intraocular lens, there arises secondary cataract in some cases; in order to prevent the progress of the secondary cataract, there is effected a treatment by an YAG laser beam; at that time, if the YAG laser beam is misapplied on the lens, the lens may develop cracks which may lead to lens breakage, etc. The intraocular lens obtained by using a crosslinking monomer, however, has a less tendency of developing cracks in the case of misapplication of YAG laser beam; moreover, the intraocular lens scarcely gives rise to dissolution of lens monomer after the YAG laser beam treatment and accordingly is superior also in chemical stability.

As specific examples of the crosslinking monomer, there can be mentioned di- or poly(meth)acrylates of diols or polyols (herein, "(meth)acrylates" refer to both acrylates and methacrylates), such as ethylene glycol dimethacrylate, triethylene glycol dimethacrylate, trimethylolpropane triacrylate, trimethylolpropane trimethacrylate, divinylbenzene, vinyl acrylate, vinyl methacrylate, allyl acrylate, allyl methacrylate, diallyl phthalate, diethylene glycol bisallylcarbonate and the like. The amount of crosslinking monomer added is preferably 0.2–10% (W/V). The reason is that when the amount is less than 0.2% (W/V), the resulting intraocular lens has no sufficient effects for the improvement of hardness, solvent resistance and resistance to YAG laser beam and, when irradiated with an YAG laser beam, gives an increased amount of monomer dissolution and; when the amount of crosslinking monomer added is more than 10% (W/V), the machinability of the resulting lens becomes lower gradually.

In the process of the present invention for producing a cyanopsia-correctable intraocular lens, the above obtained monomer solution comprising a polymerizable monomer, a colorant and a polymerization initiator as essential components and, if necessary, an U.V. absorber and/or a crosslinking monomer is preferably subjected to a filtration treatment by a filter and then is casted into a mold. The reason for preferably subjecting the monomer solution to a filtration treatment by a filter before casting into a mold is that the treatment can remove dust and bacteria. Unlike the case in which a prepolymer of high viscosity is subjected to a filtration treatment in the previously mentioned prepolymer process, the above monomer solution has a low viscosity and can be smoothly filtered even by the use of, for example, a filter having micro-fine pores of 0.2μ in pore diameter.

As the mold into which the monomer solution is casted, there can be mentioned test tubes made of a glass, a metal or a plastic chemically stable to the monomer used, such as polypropylene, polyethylene, teflon or the like, as well as molds having an intraocular lens shape and made of the same materials as above.

An intraocular lens can be obtained by subjecting the obtained polymer to lathe cut and also by melting the obtained polymer and then subjecting the molten polymer to injection or compression molding. Therefore, the shape and size of the mold into which the monomer solution is casted can be selected properly.

In the process of the present invention for producing a cyanopsia-correctable intraocular lens, the mold into which the monomer solution has been casted is then sealed and polymerization is effected to obtain a polymer. Unlike the case of the above mentioned prepolymer process, its polymerization is effected in a single step and the operation is simple.

The polymerization is effected by a means such as heating, U.V. light application or the like depending upon the kind of monomer used; however, since there are ordinarily used, as a monomer for intraocular lens, thermal polymerization type monomers which are polymerized by heating, thermal polymerization is effected generally. The conditions of thermal polymerization differ by the types of monomer and polymerization initiator used, the amount of polymerization initiator used, etc. but a stepwise or continuous temperature elevation method is employed ordinarily. In the case of a stepwise temperature elevation method, heating is effected, for example, at 30°-60° C. for 2-100 hours, at 70°-90° C. for 2-20 hours and at 100°-120° C. for 2-10 hours in this order, whereby a desired polymer is obtained. The polymer obtained is slowly cooled to 30°-60° C. in 2-24 hours, then let to cool to room temperature, and taken out from the mold.

The polymer taken out from the mold is processed into an intraocular lens using an ordinary intraocular lens processing technique.

The present invention is further explained below by way of Examples.

EXAMPLE 1

There were used 100 ml of methyl methacrylate (MMA) as a monomer capable of forming a transparent lens material upon polymerization, 0.015 g (0.015% (W/V) based on total monomer amount) of C.I. Solvent Yellow 77 as an yellow colorant, and 0.1 g (about 0.1% (W,W) based on total monomer amount) of 2,2'-azobisisobutyronitrile (AIBN) as a polymerization initiator. They were mixed to obtain a monomer solution.

The monomer solution was subjected to a filtration treatment with a membrane filter (pore diameter: 0.2μ). 20 ml of the filtrate was casted into a Pyrex test tube (inside diameter: 15 mm) used as a polymerization mold. The test tube was sealed, heated for 24 hours in a water bath of 45° C., heated in a dryer of hot air circulation type for 5 hours at 60° C., for 6 hours at 80° C. and for 6 hours at 110° C., slowly cooled to 60° C. in 6 hours, and let to cool to room temperature to obtain a bar material consisting of polymethyl methacrylate (PMMA).

Figure 9:
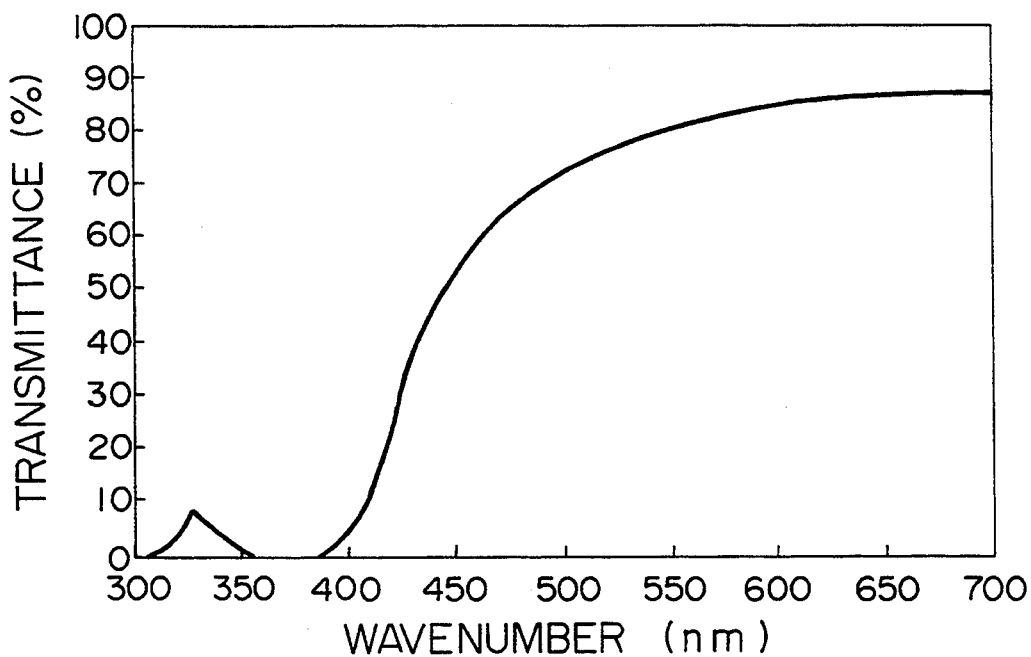
FIG. 9 is a graph showing an example of the light transmittance curve of human crystalline lens.

The bar material was processed into a button-shaped material of 8 mmφ in diameter and 3 mm in thickness. The button-shaped material was lathe-cut and polished to obtain an intraocular lens having a diameter of 6.5 mmφ, a center thickness of 1.0 mm and a refraction power of principal point in aqueous, of +20 D. The light transmittance curve of the intraocular lens was measured by an ultraviolet-visible region spectrophotometer, UV-240 manufactured by Shimadzu Corp. As shown in FIG. 1, the intraocular lens shows an absorption from 300 nm to the vicinity of 500 nm, and it became clear that the light absorption characteristic is close to that of human crystalline lens (an example of the light transmittance curve of human crystalline lens is shown in FIG. 9) and is effective for correction of cyanopsia.

EXAMPLE 2

The same procedure as in Example 1 was repeated except that 0.03% (W/V) based on total monomer amount, of C.I. Solvent Yellow 29 was used as an yellow colorant in place of the C.I. Solvent Yellow 77 used in Example 1, to obtain an intraocular lens having a diameter of 6.5 mmφ, a center thickness of 1.0 mm and a refraction power of principal point in aqueous, of +20 D.

The intraocular lens was measured for light transmittance curve in the same manner as in Example 1. The result is shown in FIG. 2. As shown in FIG. 2, the intraocular lens, similarly to the intraocular lens of Example 1, shows an absorption from 300 nm to the vicinity of 500 nm, and it became clear that the light absorption characteristic is close to that of human crystalline lens and is effective for correction of cyanopsia.

EXAMPLE 3

There were used 100 ml of methyl methacrylate (MMA) as a monomer capable of forming a transparent lens material upon polymerization, 0.015 g (0.015% (W/V) based on total monomer amount) of C.I. Yellow 77 as an yellow colorant, 0.03 g (0.03% (W/V) based on total monomer amount) of Tinuvin P (manufactured by Ciba-Geigy Corp.) as an U.V. absorber, and 0.1 g (about 0.1% (W/W) based on total monomer amount) of 2,2'-azobisisobutyronitrile (AIBN) as a polymerization initiator. They were mixed to obtain a monomer solution.

The monomer solution was subjected to a filtration treatment with a membrane filter (pore diameter: 0.2μ). 20 ml of the filtrate was casted into a Pyrex test tube (inside diameter: 15 mm) used as a polymerization mold. The test tube was sealed, heated for 24 hours in a water bath of 45° C., heated in a dryer of hot air circulation type for 5 hours at 60° C., for 6 hours at 80° C. and for 6 hours at 110° C., slowly cooled to 60° C. in 6 hours, and let to cool to room temperature to obtain a bar material consisting of polymethyl methacrylate (PMMA).

The bar material was processed into a button-shaped material of 8 mmφ in diameter and 3 mm in thickness. The button-shaped material was lathe-cut and polished to obtain an intraocular lens having a diameter of 6.5 mmφ, a center thickness of 1.0 mm and a refraction power of principal point in aqueous, of +20 D.

The light transmittance curve of the intraocular lens was measured in the same manner as in Example 1. The result is shown in FIG. 3. In the intraocular lens of Example 1 using only an yellow colorant without using any ultraviolet absorber, slight light transmittance was seen in an ultraviolet region (300-370 nm), as shown in FIG. 1. In the intraocular lens of this Example, however, complete absorption of a light in the above ultraviolet region became possible as is clear from FIG. 3. Therefore, the intraocular lens of the present Example has a light absorption characteristic closer to that of human crystalline lens and is particularly effective for correction of cyanopsia.

Figure 10:
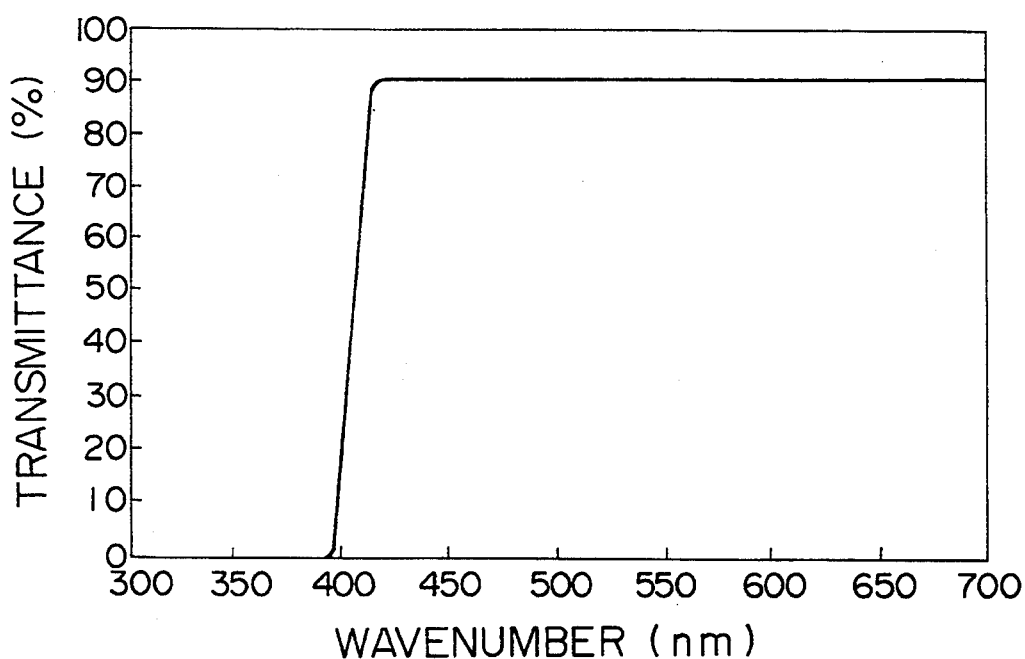
FIG. 10 is a graph showing the light transmittance curve of an intraocular lens of Comparative Example.

As a comparative example corresponding to the prior art, there was obtained an intraocular lens in the same procedure as in Example 3 except that no yellow colorant was used and 0.3% (W/V), based on total monomer amount, of Tinuvin P was used as an U.V. absorber. The light transmittance curve of this comparative intraocular lens containing a large amount of an U.V. absorber is shown in FIG. 10. As is clear from FIG. 10, in the comparative intraocular lens, although the lens contained a very large amount of an U.V. absorber, it was impossible to obtain a light transmittance curve closer to that of human crystalline lens than in Example 3.

From these results, it became clear that the intraocular lens of Example 3 can achieve a light absorption characteristic closer to that of human crystalline lens than the comparative intraocular lens, although the total amount of colorant and U.V. absorber in the lens was very small at 3/20 of the amount of U.V. abosrber in the comparative intraocular lens.

EXAMPLES 4–7

The intraocular lenses of Examples 4-7 were obtained in the same procedure as in Example 3 except that there were used the following yellow colorants and U.V. absorbers.

(Example 4)
Yellow colorant: 0.03% (W/V), based on total monomer amount, of C.I. Solvent Yellow 29
U.V. absorber: 0.03% (W/V), based on total monomer amount, of Tinuvin P (manufactured by Ciba-Geigy Corp.)

(Example 5)
Yellow colorant: 0.01% (W/V), based on total monomer amount, of C.I. Solvent Yellow 16
U.V. absorber: 0.05% (W/V), based on total monomer amount, of Tinuvin 326 (manufactured by Ciba-Geigy Corp.)

(Example 6)
Yellow colorant: 0.01% (W/V), based on total monomer amount, of C.I. Solvent Yellow 93
U.V. absorber: 0.05% (W/V), based on total monomer amount, of Tinuvin 326 (manufactured by Ciba-Geigy Corp.)

(Example 7)
Yellow colorant: 0.01% (W/V), based on total monomr amount, of C.I. Solvent Yellow 56
U.V. absorber: 0.05% (W/V), based on total monomer amount, of Tinuvin 326 (manufactured by Ciba-Geigy Corp.)

The intraocular lenses of Examples 4, 5, 6 and 7 were measured for light transmittance curve in the same manner as in Example 1. The results are shown in FIGS. 4, 5, 6 and 7, respectively.

It became clear that the light transmittance curves of the intraocular lenses of Examples 4-7 shown in FIGS. 4-7 are close to the light absorption characteristic of human crystalline lens, similarly to the case of the intraocular lens of Example 3 and are particularly effective for correction of cyanopsia.

EXAMPLE 8

An intraocular lens was obtained by using the same yellow colorant and U.V. absorber as in Example 6 but in amounts different from those in Example 6. The amount of the yellow colorant used (C.I. Solvent Yellow 93) was 0.03% (W/V) based on total monomer amount (0.01% (W/V) in Example 6), and the amount of the U.V. absorber (Tinuvin 326) was 0.03% (W/V) based on total monomer amount (0.05% (W/V) in Example 6).

Figure 8:
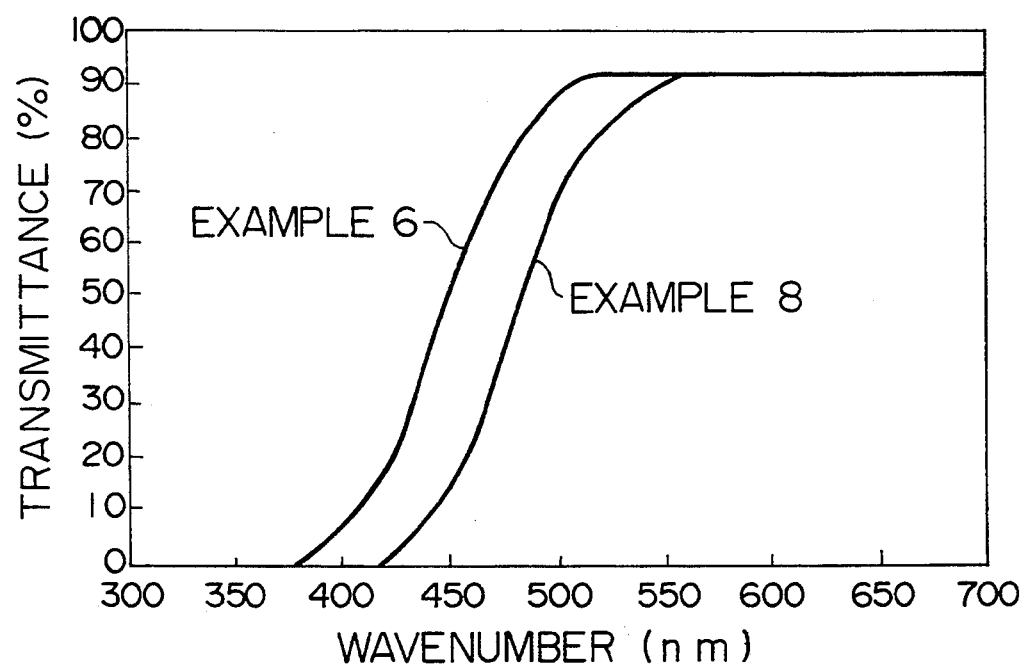

The intraocular lens was measured for light transmittance curve and the result is shown in FIG. 8. From FIG. 8, it became clear that the intraocular lens of the present Example can absorb a visible region light of 400-500 nm in a larger extent than the intraocular lens of Example 6 and that by appropriately varying the addition amounts of yellow colorant and U.V. absorber, there can be obtained various cyanopsia-correctable intraocular lenses having different light absorption characteristics. This has a very important significance when considering that the light transmittance curve of human crystalline lens changes with the aging.

EXAMPLE 9

There were used 100 ml of methyl methacrylate (MMA) as a monomer capable of forming a transparent lens material upon polymerization, 2 g (2% (W/V) based on total monomer amount) of ethylene glycol dimethacryalte (EDMA) as a crosslinking monomer, 0.01 g (0.01% (W/V) based on total monomer amount) of C.I. Solvent Yellow 93 as an yellow colorant, 0.05 g (0.05% (W/V) based on total monomer amount) of Tinuvin 326 (manufactured by Ciba-Geigy Corp.) as an U.V. absorber, and 0.1 g (about 0.1% (W/W) based on total monomer amount) of 2,2'-azobisisobutyronitrile (AIBN) as a polymerization initiator. They were mixed to obtain a monomer solution.

The monomer solution was subjected to a filtration treatment with a membrane filter (pore diameter: 0.2µ), and 20 ml of the filtrate was casted into a Pyrex test tube (inside diameter: 15 mm) used as a polymerization mold. The test tube was sealed, heated for 24 hours in a water bath of 45° C., heated in a dryer of hot air circulation type for 5 hours at 60° C., for 6 hours at 80° C. and for 6 hours at 110° C., slowly cooled to 60° C. in 6 hours, and let to cool to room temperature to obtain a bar material mainly consisting of polymethyl methacrylate (PMMA).

The bar material was processed into a button-shaped material of 8 mmφ in diameter and 3 mm in thickness. The bar-shaped material was lathe-cut and polished to obtain an intraocular lens having a diameter of 6.5 mmφ, a center thickness of 1.0 mm and a refraction power of principal point in aqueous, of +20 D.

Next, the same proceudre as in the above case using 2% (W/V) of a crosslinking monomer was repeated except that the amount of crosslinking monomer was changed to 0.2% (W/V), 10.0% (W/V) and 15.0% (W/V) based on total monomer amount, to additionally obtain three different intraocular lenses.

The total four intraocular lenses obtained were confirmed to each have a light absorption characteristic close to that of human crystalline lens and be effective as a cyanopsia-correctable intraocular lens.

Further, these four intraocular lenses were tested for harndess, solvent resistance, machinability, resistnace to Nd:YAG laser beam, and dissolution of monomer, colorant or U.V. absorber due to application of Nd:YAG laser beam. The results are shown in Table 1 together with the results of the intraocular lens containing no crosslinking monomer (the lens corresponding to the intraocular lens of Example 1).

As is clear from Table 1, it was confirmed that the addition of crosslinking monomer in an amount of 0.2–15% (W/V) significantly improves hardness, solvent resistance and resistance to Nd:YAG laser beam and significantly reduces the dissolution of monomer due to application of Nd:YAG laser beam, as compared with the case of no addition of crosslinking monomer.

It also became clear that machinability is satisfactory when the amount of crosslinking monomer added is 10.0% (W/V) or less.

serious when viewed as a physical damage of lens and, in some cases, lead to lens breakage.

(5) Dissolution of monomer, etc. due to application of Nd:YAG laser beam

A test piece consisting of a disc of 12 mm$\phi$ in diameter and 1 mm in thickness was placed in a 5-ml cell for spectrophotometer, together with 4 ml of purified water. To the surface of the test piece was applied a Nd:YAG laser beam 100 times at a power of 10 mJ (millijoule). After the application, the test piece was taken out and the absorbance at the maximum absorption wavelength (206 nm) of the monomer was mea-

TABLE 1

|  |  | Example 1 |  |  | Example 9 |  |
|---|---|---|---|---|---|---|
| Amount of crosslinking monomer added [% (W/V)] |  | 0 | 0.2 | 2 | 10.0 | 15.0 |
| Hardness |  | 95 | 98 | 100 | 103 | 103 |
| Solvent resistance |  | Poor (soluble) | Good (insoluble) | Good (insoluble) | Good (insoluble) | Good (insoluble) |
| Machinability |  | ⊚ | ⊚ | ⊚ | ○ | Δ |
| Resisiance to ND:YAG laser beam |  | Cracks appeared. | Pits appeared, but no crack appeared and the lenses were little affected optically. | | | |
| Dissolution due to application of Nd:YAG laser beam | Amount of monomer dissolved | 2.47 μg | 1.52 μg | 1.24 μg | 1.18 μg | 1.20 μg |
|  | Amount of colorant dissolved | Not detectable at a detection limit of 0.007 ppm. | | | | |
|  | Amount of U.V. absorber dissolved | — | Not detectable at a detection limit of 0.007 ppm. | | | |

The test methods of various properties shown in Table 1 are as follow.

(1) Hardness

Measured in accordance with JIS K 7202, using a test piece consisting of a disc of 15 mm$\phi$ in diameter and 5 mm in thickness.

(2) Solvent resistance 0.5 g of a ground sample was placed in an Erlenmeyer flask with stopper; 50 ml of benzene was added; the mixture was allowed to stand for 5 days at room temperature with shaking at given time intervals; and the condition of dissolution of the sample was observed. The sample was rated as "good" in solvent resistance when it was insoluble and as "poor" in solvent resistance when it was soluble.

(3) Machinability

The surface condition after lathe cut was observed with a mangifier of 40 magnification to examine the extent of small defects and lathe marks on the surface. An excellent surface condition was expressed as ⊚, a good surface condition as , and a poor surface condition as Δ.

(4) Resistance to Nd:YAG laser beam

A Nd:YAG laser beam having a power of 2 mJ (millijoule) was allowed to hit the posterior surface of an intraocular lens and then the change of the intraocular lens was observed with a magnifier. The change of the intraocular lens after application of Nd:YAG laser beam is rated in two items of pits and cracks. The pits are through-holes generated in the lens and characteristic of laser beam application. Each through-hole per se is extremely small and accordingly hardly affects the optical properties of the lens. Meanwhile, the cracks refer to not only the generation of through-holes in the lens but also the secondary change of the lens material in the neighborhood of the through-holes. The intraocular lens having cracks retain no optical properties required for lenses, in many cases. Further, the cracks are sured by a spectrophotometer. Using a calibration curve prepared beforehand, there was calculated the amount of monomer [in terms of MMA (unit: μg)] dissolved in water owing to the application of the Nd:YAG laser beam.

With respect to the colorant and the U.V. absorber, there were measured absorbances at the respective maximum absorption wavelengths (detection limit: 0.007 ppm).

As illustrated also in Examples, according to the present invention there has been provided a process for producing a cyanopsia-correctable intraocular lens, which lens is able to effectively correct the cyanopsia arising in aphakic eye patients after operation of cataract.

According to the present invention there has also been provided a process for producing a cyanopsia correctable intraocular lens, which process is able to obtain smoothly without requiring a complicated operation, an intraocular lens capable of effectively correcting the above cyanopsia.

We claim:

1. A process for producing a cyanopsia-correctable intraocular lens by monomer cast polymerization which comprises:
   (a) casting into a mold a monomer solution consisting essentially of methylmethacrylate capable of forming a transparent lens material upon polymerization, at least one colorant selected from the group consisting of C.I. Solvent Yellow 16, C.I. Solvent Yellow 29, C.I. Solvent Yellow 56, C.I. Solvent Yellow 77, and C.I. Solvent Yellow 93, and a polymerization initiator;
   (b) sealing the mold; and
   (c) polymerizing the monomer solution to produce a cyanopsia-correctable intraocular lens which is devoid of ultraviolet absorbers.

2. The process according to claim 1, wherein the amount of the colorant is 0.01–0.05% (W/V) based on total monomer amount.

3. The process according to claim 2, wherein the amount of the colorant is 0.01–0.03% (W/V) based on total monomer amount.

4. The process according to claim 1, wherein the monomer solution also contains a crosslinking monomer.

5. The process according to claim 4, wherein the amount of the crosslinking monomer is 0.2–10% (W/V) based on total monomer amount.

6. The process according to claim 1, wherein the polymerization initiator is an azo polymerization initiator.

7. The process according to claim 6, wherein the amount of the azo polymerization initiator is 0.01–1.09% (W/W) based on total monomer amount.

8. The cyanopsia-correctable intraocular lens produced by the process of claim 1.

9. A process for producing a cyanopsia-correctable intraocular lens by monomer cast polymerization which process comprises the steps of:
  (a) casting into a mold a monomer solution consisting essentially of methylmethacrylate capable of forming a transparent lens material upon polymerization, a polymerization initiator, an ultraviolet absorber and at least one colorant selected from the group consisting of C.I. Solvent Yellow 16, C.I. Solvent Yellow 29, C.I. Solvent Yellow 56, C.I. Solvent Yellow 77, and C.I. Solvent Yellow 93;
  (b) sealing the mold; and
  (c) polymerizing the monomer solution to produce a cyanopsia-correctable intraocular lens.

10. The process according to claim 9, wherein the amount of the colorant is 0.01–0.05% (W/V) based on total monomer amount.

11. The process according to claim 9, wherein the amount of the colorant is 0.01–0.03% (W/V) based on total monomer amount and the amount of the U.V. absorber is 0.03–0.05% (W/V) based on total monomer amount.

12. The process according to claim 9, wherein the monomer solution also contains a crosslinking monomer.

13. The process according to claim 11, wherein the amount of the crosslinking monomer is 0.2–10% (W/V) based on total monomer amount.

14. The process according to claim 9, wherein the polymerization initiator is an azo polymerization initiator.

15. The process according to claim 13, wherein the amount of the azo polymerization initiator is 0.01–1.09% (W/W) based on total monomer amount.

16. The cyanopsia-correctable intraocular lens produced by the process of claim 9.

* * * * *